United States Patent
Deng et al.

(10) Patent No.: US 10,067,112 B2
(45) Date of Patent: Sep. 4, 2018

(54) AUTONOMOUS SENSOR FISH TO SUPPORT ADVANCED HYDROPOWER DEVELOPMENT

(71) Applicant: Battelle Memorial Institute, Richland, WA (US)

(72) Inventors: Z. Daniel Deng, Richland, WA (US); Mitchell J. Myjak, Richland, WA (US); Jun Lu, Richland, WA (US); Jayson J. Martinez, Richland, WA (US); Chuan Tian, Richland, WA (US); Thomas J. Carlson, Holmes Beach, FL (US); Scott J. Morris, Kennewick, WA (US); Hongfei Hou, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 18 days.

(21) Appl. No.: 14/871,761

(22) Filed: Sep. 30, 2015

(65) Prior Publication Data
US 2017/0089878 A1    Mar. 30, 2017

(51) Int. Cl.
| E02B 8/00 | (2006.01) |
|---|---|
| G01N 33/18 | (2006.01) |
| G01F 22/00 | (2006.01) |
| E02B 8/08 | (2006.01) |
| E02B 1/00 | (2006.01) |

(52) U.S. Cl.
CPC ......... *G01N 33/1886* (2013.01); *G01F 22/00* (2013.01); *E02B 1/00* (2013.01); *E02B 8/08* (2013.01); *E02B 8/085* (2013.01); *E02B 2201/00* (2013.01)

(58) Field of Classification Search
None
See application file for complete search history.

(56) References Cited

U.S. PATENT DOCUMENTS
| 3,100,866 A | 8/1963 | Marks |
|---|---|---|
| 3,262,093 A | 7/1966 | Junger et al. |

(Continued)

FOREIGN PATENT DOCUMENTS
| CA | 2091043 | 9/1994 |
|---|---|---|
| CN | 2014800479315 | 9/1994 |

(Continued)

OTHER PUBLICATIONS

Carlson et al., "Juvenile Salmon Acoustic Telemetry System Transmitter Downsize Assessment", Pacific Northwest National Laboratory, Richland, WA, 2010, United States, 30 pages.

(Continued)

*Primary Examiner* — Jill Culler
(74) *Attorney, Agent, or Firm* — Wells St. John P.S.

(57) ABSTRACT

An improved sensor fish with robust design and enhanced measurement capabilities. This sensor fish contains sensors for acceleration, rotation, magnetic field intensity, pressure, and temperature. A low-power microcontroller collects data from the sensors and stores up to 5 minutes of data on a non-volatile flash memory. A rechargeable battery supplies power to the sensor fish. A recovery system helps locating sensor fish. The package, when ready for use is nearly neutrally buoyant and thus mimics the behavior of an actual fish.

13 Claims, 7 Drawing Sheets

(56) References Cited

U.S. PATENT DOCUMENTS

| | | | |
|---|---|---|---|
| 3,311,830 A | 3/1967 | Skirvin | |
| 3,576,732 A | 4/1971 | Weidinger et al. | |
| 3,713,086 A | 1/1973 | Trott | |
| 4,042,845 A | 8/1977 | Hackett | |
| 4,241,535 A * | 12/1980 | Tsukuda | A63H 23/04 |
| | | | 446/156 |
| 4,259,415 A | 3/1981 | Tamura et al. | |
| 4,353,004 A | 10/1982 | Kleinschmidt | |
| 4,762,427 A | 8/1988 | Hori et al. | |
| 4,986,276 A | 1/1991 | Wright | |
| 5,177,891 A * | 1/1993 | Holt | A01K 79/02 |
| | | | 43/17.1 |
| 5,211,129 A | 5/1993 | Taylor et al. | |
| 5,344,357 A * | 9/1994 | Lyczek | A63H 23/10 |
| | | | 446/154 |
| 5,517,465 A * | 5/1996 | Nestler | G10K 11/006 |
| | | | 119/174 |
| 5,675,555 A * | 10/1997 | Evans | G01P 1/127 |
| | | | 367/139 |
| 5,697,384 A | 12/1997 | Miyawaki et al. | |
| 5,974,304 A | 10/1999 | Chen | |
| 5,995,451 A * | 11/1999 | Evans | G01H 3/00 |
| | | | 367/139 |
| 6,201,766 B1 * | 3/2001 | Carlson | H04R 23/00 |
| | | | 367/141 |
| 6,662,742 B2 * | 12/2003 | Shelton | F16M 11/125 |
| | | | 114/312 |
| 6,712,772 B2 | 3/2004 | Cohen et al. | |
| 7,016,260 B2 | 3/2006 | Bary | |
| 7,289,931 B2 | 10/2007 | Ebert | |
| 7,457,720 B2 | 11/2008 | Ebert | |
| 8,032,429 B2 | 10/2011 | Shafer | |
| 8,033,890 B2 * | 10/2011 | Warner | A63H 23/04 |
| | | | 446/161 |
| 8,485,985 B2 | 6/2013 | Nagano et al. | |
| 9,266,591 B2 * | 2/2016 | Lu | A63H 33/26 |
| 2003/0117893 A1 | 6/2003 | Bary | |
| 2003/0128847 A1 | 7/2003 | Smith | |
| 2006/0218374 A1 | 9/2006 | Ebert | |
| 2007/0088194 A1 | 4/2007 | Tahar et al. | |
| 2007/0103314 A1 | 5/2007 | Giessler | |
| 2007/0288160 A1 | 12/2007 | Ebert | |
| 2009/0073802 A1 | 3/2009 | Nizzola et al. | |
| 2009/0079368 A1 | 3/2009 | Poppen et al. | |
| 2009/0188320 A1 | 7/2009 | Greenough et al. | |
| 2011/0105829 A1 | 5/2011 | Ball | |
| 2011/0163857 A1 | 7/2011 | August et al. | |
| 2011/0181399 A1 | 7/2011 | Pollack et al. | |
| 2011/0254529 A1 | 10/2011 | van Straaten | |
| 2012/0134239 A1 | 5/2012 | Struthers | |
| 2012/0277550 A1 | 11/2012 | Rosenkranz et al. | |
| 2013/0012865 A1 | 1/2013 | Sallberg et al. | |
| 2013/0181839 A1 | 7/2013 | Cao | |
| 2013/0324059 A1 | 12/2013 | Lee et al. | |
| 2014/0211594 A1 | 7/2014 | Allen et al. | |
| 2015/0063072 A1 | 3/2015 | Deng et al. | |
| 2015/0241566 A1 | 8/2015 | Chakraborty et al. | |
| 2015/0289479 A1 | 10/2015 | Allen et al. | |
| 2016/0211924 A1 | 7/2016 | Deng et al. | |
| 2016/0245894 A1 | 8/2016 | Deng et al. | |
| 2017/0164581 A1 | 6/2017 | Deng et al. | |
| 2017/0170850 A1 | 6/2017 | Deng et al. | |
| 2018/0055007 A1 | 3/2018 | Deng et al. | |

FOREIGN PATENT DOCUMENTS

| | | |
|---|---|---|
| CN | 1424592 | 6/2003 |
| CN | 102568463 | 7/2012 |
| CN | 102598716 | 7/2012 |
| CN | 202414143 | 9/2012 |
| CN | 102754249 | 10/2012 |
| EP | 2037396 A1 | 3/2009 |
| EP | 1705500 B1 | 6/2010 |
| GB | 1195633 A | 6/1970 |
| GB | 2188028 A | 9/1987 |
| WO | WO 95/03691 | 2/1995 |
| WO | WO 2011/068825 | 6/2011 |
| WO | WO 2011/079338 | 7/2011 |
| WO | WO PCT/US2014/053578 | 12/2014 |
| WO | WO 2015/031853 | 3/2015 |
| WO | WO PCT/US2014/053578 | 3/2015 |
| WO | WO PCT/US2014/053578 | 3/2016 |
| WO | WO PCT/US2016/054981 | 11/2016 |
| WO | WO PCT/US2016/055045 | 2/2017 |
| WO | WO PCT/US2015/062200 | 8/2017 |
| WO | WO PCT/US2017/038082 | 9/2017 |
| WO | WO PCT/US2017/038082 | 11/2017 |

OTHER PUBLICATIONS

El Rifai et al., "Modeling of Piezoelectric Tube Actuators", Dspace@MIT: Innovation in Manufacturing Systems and Technology (IMST), 2004, Singapore, 9 pages.

Pacific Northwest National Laboratory, "JSATS Tag Downsize Project Progress Report", PNNL, Apr. 26, 2010, United States, 16 pages.

Pacific Northwest National Laboratory, "Juvenile Salmon Acoustic Telemetry System (JSATS) Acoustic Transmitters", PNNL, Mar. 2010, United States, 1 page.

Butler et al., "A Tri-Modal Directional Modem Transducer", Oceans 2003 MTS/IEEE Conference, Sep. 22-26, 2003, United States, pp. 1554-1560.

Lewandowski et al., "In Vivo Demonstration of a Self-Sustaining, Implantable, Stimulated-Muscle-Powered Piezoelectric Generator Prototype", Annals of Biomedical Engineering vol. 37, No. 11, Nov. 2009, Netherlands, pp. 2390-2401.

Platt et al., "The Use of Piezoelectric Ceramics for Electric Power Generation Within Orthopedic Implants", IEEE/ASME Transactions on Mechatronics vol. 10, No. 4, Aug. 2005, United States, pp. 455-461.

Rifai et al., "Modeling of Piezoelectric Tube Actuators", Dspace@MIT, available online at https://dspace.mit.edu/bitstream/handle/1721.1/3911/IMST014.pdf, 2004, 8 pages.

Brown, "Design Considerations for Piezoelectric Polymer Ultrasound Transducers", IEEE Transactions on Ultrasonics, Ferroelectrics, and Frequency Control vol. 47, No. 6, Nov. 2000, United States, pp. 1377-1396.

Brown, "The Effects of Material Selection for Backing and Wear Protection/Quarter-Wave Matching of Piezoelectric Polymer Ultrasound Transducers", IEEE Ultrasonics Symposium, 2000, United States, pp. 1029-1032.

Cada, "The Development of Advanced Hydroelectric Turbines to Improve Fish Passage Survival", Fisheries vol. 26, No. 9, Sep. 2001, United States, pp. 14-23.

Carlson et al., "Sensor Fish Characterization of Spillway Conditions at Ice Harbor Dam in 2004, 2005 and 2006", PNWD-3839 Final Report, Mar. 2008, United States, 95 pages.

Carlson et al., "The Sensor Fish—Making Dams More Salmon-Friendly", Sensors Online, Jul. 2004, United States, 7 pages.

Coutant, "Fish Behavior in Relation to Passage Through Hydropower Turbines: A Review", Transactions of the American Fisheries Society vol. 129, 2000, United States, pp. 351-380.

Deng et al., "Design and Implementation of a New Autonomous Sensor Fish to Support Advanced Hydropower Development", Review of Scientific Instruments vol. 85, 2014, United States, 6 pages.

Deng et al., "Evaluation of Fish-Injury Mechanisms During Exposure to Turbulent Shear Flow", Canadian Journal of Fisheries and Aquatic Sciences vol. 62, 2005, Canada, pp. 1513-1522.

(56) References Cited

OTHER PUBLICATIONS

Deng et al., "Six-Degree-of-Freedom Sensor Fish Design and Instrumentation", Sensors vol. 7, 2007, United States, pp. 3399-3415.

Deng et al., "Use of an Autonomous Sensor to Evaluate the Biological Performance of the Advanced Turbine at Wanapum Dam", Journal of Renewable and Sustainable Energy vol. 2, 2010, United States, 11 pages.

Johnson et al., "A Digital Acoustic Recording Tag for Measuring the Response of Wild Marine Mammals to Sound", IEEE Journal of Oceanic Engineering vol. 28, No. 1, Jan. 2003, United States, pp. 3-12.

Kogan et al., "Acoustic Concentration of Particles in Piezoelectric Tubes: Theoretical Modeling of the Effect of Cavity Shape and Symmetry Breaking", The Journal of the Acoustical Society of America vol. 116, No. 4, 2004, United States, pp. 1967-1974.

Odeh, "A Summary of Environmentally Friendly Turbine Design Concepts", DOE/ID/13741 Paper, Jul. 1999, United States, 47 pages.

Richmond et al., "Response Relationships Between Juvenile Salmon and an Autonomous Sensor in Turbulent Flow", Fisheries Research vol. 97, 2009, Netherlands, pp. 134-139.

Aktakka et al., "Energy Scavenging from Insect Flight", Journal of Micromechanics and Microengineering vol. 21, 095016, 2011, United Kingdom, 10 pages.

Brown et al., "An Evaluation of the Maximum Tag Burden for Implantation of Acoustic Transmitters in Juvenile Chinook Salmon", North American Journal of Fisheries Management vol. 30, 2010, United States, pp. 499-505.

Cha et al., "Energy Harvesting from a Piezoelectric Biomimetic Fish Tail", Renewable Energy vol. 86, 2016, Netherlands, pp. 449-458.

Cha et al., "Energy Harvesting from the Tail Beating of a Carangiform Swimmer using Ionic Polymer-Metal Composites", Bioinspiration and Biomimetics vol. 8, 2013, United Kingdom, 15 pages.

Cook et al., "A Comparison of Implantation Methods for Large PIT Tags or Injectable Acoustic Transmitters in Juvenile Chinook Salmon", Fisheries Research vol. 154, 2014, Netherlands, pp. 213-223.

Dagdeviren et al., "Conformal Piezoelectric Energy Harvesting and Storage from Motions of the Heart, Lung, and Diaphragm", Proceedings of the National Academy of Sciences of the United States of America vol. 111, 2014, United States, pp. 1927-1932.

Deng et al., "A Cabled Acoustic Telemetry System for Detecting and Tracking Juvenile Salmon: Part 2, Three-Dimensional Tracking and Passage Outcomes", Sensors vol. 11, 2011, Switzerland, pp. 561-5676.

Deng et al., "An Injectable Acoustic Transmitter for Juvenile Salmon", Scientific Reports, Jan. 29, 2015, United Kingdom, 6 pages.

Deng et al., "Design and Instrumentation of a Measurement and Calibration System for an Acoustic Telemetry System", Sensors vol. 10, 2010, Switzerland, pp. 3090-3099.

Deng et al., U.S. Appl. No. 15/087,936, filed Mar. 31, 2016, titled "Signal Transmitter and Methods for Transmitting Signals from Animals", 59 pages.

Deng et al., U.S. Appl. No. 62/267,738, filed Dec. 15, 2015, titled "Transmitters for Animals and Methods for Transmitting from Animals", 42 pages.

Eppard, "Juvenile Salmon Acoustic Telemetry System JSATS", Dec. 14, 2011, URL: http://www.nwcouncil.org/media/23478/jsats.pdf, pp. 1-13.

Erturk et al., "Underwater Thrust and Power Generation Using Flexible Piezoelectric Composites: An Experimental Investigation Toward Self-Powered Swimmer-Sensor Platforms", Smart Materials and Structures vol. 20, 125013, 2011, United Kingdom, 11 pages.

Hwang et al., "Self-Powered Cardiac Pacemaker Enabled by Flexible Single Crystaline PMN-PT Piezoelectric Energy Harvester", Advanced Materials vol. 26, 2014, Germany, pp. 4880-4887.

Hwang et al., "Self-Powered Deep Brain Stimulation via a Flexible PIMNT Energy Harvester", Energy and Environmental Science vol. 8, 2015, United Kingdom, pp. 2677-2684.

Lam et al., "Physical Characteristics and Rate Performance of $(CFx)n$ $(0.33<x<9,66)$ in Lithium Batteries", Journal of Power Sources vol. 153, 2006, Netherlands, pp. 354-359.

Li et al., "Design Parameters of a Miniaturized Piezoelectric Underwater Acoustic Transmitter", Sensors vol. 12, 2012, Switzerland, pp. 9098-9109.

Li et al., "Energy Harvesting from Low Frequency Applications using Piezoelectric Materials", Applied Physics Reviews 1, 041301, 2014, United States, 20 pages.

Li et al., "Piezoelectric Materials Used in Underwater Acoustic Transducers" Sensor Letters vol. 10 (3/4), 2012, United States, pp. 679-697.

Li et al., "Piezoelectric Transducer Design for a Miniaturized Injectable Acoustic Transmitter", Smart Materials and Structures vol. 24, 115010, 2015, United Kingdom, 9 pages.

McMichael et al., "The Juvenile Salmon Acoustic Telemetry System: A New Tool", Fisheries vol. 35, No. 1, Jan. 1, 2010, United States, pp. 9-22.

Meduri et al., "Hybrid $CVx-Ag2V4O11$ as a High-Energy, Power Density Cathode for Application in an Underwater Acoustic Microtransmitter", Electrochemistry Communications vol. 13, 2011, United States, pp. 1344-1348.

Ritchie et al., "Further Developments of Lithium/Polycarbon Monofluoride Envelope Cells", Journal of Power Sources vol. 96, 2001, Netherlands, pp. 180-183.

Rub et al., "Comparative Performance of Acoustic-Tagged and Passive Integrated Transponder-Tagged Juvenile Salmonids in the Columbia and Snake Rivers", U.S. Army Corps of Engineers, Portland District, Portland Oregon, 2007, United States, 163 pages.

S.M. Corporation, "Macro Fiber Composite—MFC" Smart Material Brochure, United States, 8 pages.

Shafer, "Energy Harvesting and Wildlife Monitoring", available online at http://www.ofwim.org/wp-content/uploads/2014/11/Shafer_keynote.pdf, 2014, 36 pages.

Weiland et al., "A Cabled Acoustic Telemetry System for Detecting and Tracking Juvenile Salmon: Part 1. Engineering Design and Instrumentation", Sensors vol. 11, No. 12, Dec. 26, 2011, Switzerland, pp. 5645-5660.

Yazami et al., "Fluorinated Carbon Nanofibres for High Energy and High Power Densities Primary Lithium Batteries", Electrochemistry Communications vol. 9, 2007, United States, pp. 1850-1855.

Zhang et al., "Enhancement of Discharge Performance of $Li/CFx$ Cell by Thermal Treatment of $CFx$ Cathode Material", Journal of Power Sources vol. 188, 2009, Netherlands, pp. 601-605.

Deng et al., U.S. Appl. No. 15/088,032, filed Mar. 31, 2016, titled "Transmitters for Animals and Methods for Transmitting from Animals", 57 pages.

Deng et al., U.S. Appl. No. 62/267,797, filed Dec. 15, 2015, titled "Signal Transmitter and Methods for Transmitting Signals from Animals", 34 pages.

Dillon, "Use and Calibration of the Internal Temperature Indicator", Microchip Technology Inc. AN1333, 2010, United States, 12 pages.

Adams et al., "Effects of Surgically and Gastrically Implanted Radio Transmitters on Swimming Performance and Predator Avoidance of Juvenile Chinook Salmon (Oncorhynchus tshawytscha)", Canadian Journal of Fisheries and Aquatic Sciences 55, 1998, Canada, pp. 781-787.

Anglea et al., "Effects of Acoustic Transmitters on Swimming Performance and Predator Avoidance of Juvenile Chinook Salmon", North American Journal of Fisheries Management 24, 2004, United States, pp. 162-170.

Atlantic States Marine Fisheries Commission, "American Eel Benchmark Stock Assessment Report No. 12-01", May 2012, United States, 340 pages.

Barns, "Differences in Performance of Naturally and Artificially Propagated Sockeye Salmon Migrant Fry, as Measured with Swim-

(56) References Cited

OTHER PUBLICATIONS ming and Predation Tests", Journal of the Fisheries Board of Canada 24(5), 1967, Canada, pp. 1117-1153.
Barbin et al., "Behaviour and Swimming Performance of Elvers of the American Eel, Anguilla rostrata, in an Experimental Flume", Journal of Fish Biology 45, 1994, United Kingdom, pp. 111-121.
Biopack Systems, Inc. Hardware Guide, 2013, 152 pages.
Boubee et al., "Downstream Passage of Silver Eels at a Small Hydroelectric Facility", Fisheries Management and Ecology vol. 13, 2006, United Kingdom, pp. 165-176.
Brett, "The Respiratory Metabolism and Swimming Performance of Young Sockeye Salmon", Journal of the Fisheries Board of Canada 21(5), 1964, Canada, pp. 1183-1226.
Brown et al., "Evidence to Challenge the "2% Rule" for Biotelemetry", North American Journal of Fisheries Management 19, 1999, United States, pp. 867-871.
Brown et al., "Survival of Seaward-Migrating PIT and Acoustic-Tagged Juvenile Chinook Salmon in the Snake and Columbia Rivers: An Evaluation of Length-Specific Tagging Effects", Animal Biotelemetry 1:8, 2013, United States, 13 pages.
Collins et al., "Intracoelomic Acoustic Tagging of Juvenile Sockeye Salmon: Swimming Performance, Survival, and Postsurgical Wound Healing in Freshwater and during a Transition to Seawater", Transactions of the American Fisheries Society 142, 2013, United States, pp. 515-523.
Cote et al., "Swimming Performance and Growth Rates of Juvenile Atlantic Cod Intraperitoneally Implanted with Dummy Acoustic Transmitters", North American Journal of Fisheries Management vol. 19, 1999, United States, pp. 1137-1141.
Counihan et al., "Influence of Externally Attached Transmitters on the Swimming Performance of Juvenile White Sturgeon", Transactions of the American Fisheries Society 128, 1999, United States, pp. 965-970.
Deng et al., U.S. Appl. No. 15/393,617, filed Dec. 29, 2016, titled "Systems and Methods far Monitsring Organisms Within an Aquatic Environment", 49 pages.
Dinwoodie, "Dual Output Boost Converter", Texas Instruments Application Report SLUA288, available online at http://www.ti.com/lit/an/slua288/slua288.pdf, Apr. 2003, 9 pages.
Fisheries and Oceans Canada (DFO), "Recovery Patentiai Assessment of American Eel (Anguilla rostrata) in Eastern Canada", Canadian Science Advisory Segretariat Science Advisory Report 2013/078, 2013, Canada, 65 pages.
Gallego-Juarez et al., "Experimental Study of Nonlinearity in Free Progressive Acoustic Waves in Air at 20 kHz", Journal de Physique, Colloques, 40 (C8), 1979, France, pp. 336-340.
Harnish et al., "A Review of Polymer-Based Water Conditioners for Reduction of Handling-Related Injury", Reviews in Fish Biology and Fisheries 21, 2011, Netherlands, pp. 43-49.
Janak et al., "The Effects of Neutrally Buoyant, Externally Attached Transmitters on Swimming Performance and Predatar Avoidance of Juvenile Chinook Salmon", Transactians of the American Fisheries Society 141, 2012, United States, pp. 1424-4432.

Li et al., "Piezoelectric Materials used in Underwater Acoustic Transmitters", Sensor Letters vol. 10, 2012, United States, 65 pages.
MacGregor et al., "Recovery Strategy for the American Eel (Anguilla rostrata) in Ontario", Ontario Recovery Strategy Series, Prepared for Ontario Ministry of Natural Resources, Peterborough, Ontario, 2013, Canada, 131 pages.
McGrath et al., "Studies of Upstream Migrant American Eels at the Moses-Saunders Power Dam on the St. Lawrence River near Massena, New York", American Fisheries Society Symposium 33, 2003, United States, pp. 153-166.
Mesa et al., "Survival and Growth of Juvenile Pacific Lampreys Tagged with Passive Integrated Transponders (PIT) in Freshwater and Seawater", Transactions of the American Fisheries Society 141, 2012, United States, pp. 1260-1268.
Mueller et al., "Tagging Juvenile Pacific Lamprey with Passive Integrated Transponders: Methodology Short-Term Mortality, and Influence on Swimming Performance", North American Journal of Fisheries Management vol. 26, 2006, United States, pp. 361-366.
Normandeau, "Survey for Upstream American Eel Passage at Holyoke Dam, Connecticut River, Massachusetts, 2006", Prepared for Holyoke Gas and Electric by Normandeau Associates, Inc., Apr. 26, 2007, United States, 68 pages.
Økland et al., "Recommendations on Size and Position of Surgically and Gastrically Implanted Electronic Tags in European Silver Eel", Animal Biotelemetry 1:6, 2013, United Kingdom. pp. 1-5.
Panther et al., "Influence of Incision Location on Transmitter Loss, Healing, Survival, Growth, and Suture Retention of Juvenile Chinook Salmon", Transactions of the American Fisheries Society 140, 2011, United States, pp. 1492-1503.
Summerfelt et al., "Anesthesia, Surgery, and Related Techniques", in Schreck, C.B., Moyle, P.B., (Eds.), Methods for Fish Biology, American Fisheries Society, 1990, United States, pp. 213-272.
Verdon et al., "Recruitment of American Eels in the Richelieu River and Lake Champlain: Provision of Upstream Passage as a Regional-Scale Solution to a Large-Scale Problem", American Fisheries Society Symposium 33, 2003, United States, pp. 125-138.
Walker et al., "Effects of a Novel Acoustic Transmitter on Swimming Performance and Predator Avoidance of Juvenile Chinook Salmon: Determination of a Size Threshold", Fisheries Research 176, Apr. 2016, Netherlands, pp. 48-54.
Ward et al , "A Laboratory Evaluation of Tagging-Related Mortatlity and Tag Loss in Juvenile Humpback Chub", North American Journal of Fisheries Management 35, 2015, United States, pp. 135-140.
Wuenschel et al., "Swimming Ability of Eels (Anguilla rostrata, Conger oceanicus) at Estuarine Ingress: Contrasting Patterns of Cross-Shelf Transport?", Marine Biology 154, 2008, Germany, pp. 775-786.
Zales et al., "Effects of Surgically Implanted Transmitter Weights on Growth and Swimming Stamina of Small Adult Westslope Cutthroat Trout", Transactions of the American Fisheries Society vol 134(3), 2005, United States, pp. 653-660.

\* cited by examiner

AUTONOMOUS SENSOR FISH TO SUPPORT ADVANCED HYDROPOWER DEVELOPMENT

STATEMENT AS TO RIGHTS TO INVENTIONS MADE UNDER FEDERALLY-SPONSORED RESEARCH AND DEVELOPMENT

This invention was made with Government support under Contract DE-AC0576RLO1830 awarded by the U.S. Department of Energy. The Government has certain rights in the invention.

BACKGROUND OF THE INVENTION

Field of the Invention

The invention generally relates to environmental sensors and more particularly to sensors utilized in hydro dams or other hydraulic structures to assess the forces encountered by fish passing through such dams and other structures and characterize complex flow field.

Background Information

Fish passing through hydroturbines or other hydraulic structures may be injured or killed when they are exposed to the severe hydraulic conditions found therein. Such conditions could include rapid and extreme pressure changes, shear stress and turbulence, strike by runner blades and cavitation. In building new dams and as existing turbines near the end of their operational life and are set to be replaced, new designs for runners and other portions of the turbine system are being considered. As part of this effort, in the Pacific Northwest and elsewhere, improved survival rates and reduced injury rates for fish passing through turbines are being considered as design parameters. To create these designs, data is needed to understand the environment through which the fish were required to pass.

Studies using live fish are useful for the evaluation of dams' biological performance, but are limited in that they cannot determine the specific hydraulic conditions or physical stresses experienced by the fish, the locations where deleterious conditions occur, or the specific causes of the biological response. To overcome this deficiency, various other sensor devices have been developed. These devices can be released independently or concurrently with live fish directly into operating turbines or other passage routes as a means of measuring hydraulic conditions such as pressure, acceleration, and rotation acting on a body in situ during downstream passage. These early devices were originally designed for the large Kaplan turbines in the Columbia River basin and were used by the U.S. Army Corps of Engineers, who collaborated with the U.S. Department of Energy for its development, for virtually all of their post-construction structural and operations fish passage evaluations at mainstem Columbia River dams. Correlation metrics between these early sensor measurements and live fish injuries were also developed by conducting concurrent releases in turbulent shear flows under controlled laboratory conditions.

While useful in their time, these types of devices have tended to lack the sufficient robustness required to survive the rapidly changing and extreme conditions within the testing sites. In addition the speed at which conditions change made most of these sensors less useful because they were not able to acquire information in rapid fashion so as to give the true account of the significant changes that took place in the bodies of these fish as they passed through these environments. The size, functional limitations and problems with deployment and recovery, availability, and cost of these prior art devices have limited its use beyond the main stem Columbia River and its original application. As newer designs for turbines, dams, and pumping stations provide new and unknown conditions that the existing sensor devices cannot tolerate and which may not adequately reflect and report the conditions to which it is subjected.

Desirable devices overcome some of these limitations; they can be robust, cost accessible, as well as provide rapid data acquisition and be more widely deployable and be operable in more severe hydraulic conditions including but not limited to high-head dams with Francis turbines and pump storage facilities. Additionally, desirable devices can have outputs that can be more readily read and understood than the existing processes for the old devices.

The present disclosure provides sensor fish with more capabilities that can accelerate conventional hydropower development by shortening schedules and decreasing costs for validation of performance claims to regulators, and by providing feedback to design engineers about many of the hydro-turbine designs and environmental settings being considered to increase power generation. The sensor fish and utilization thereof can, lower the procurement and deployment costs which can be important for increasing the accessibility and acceptance of this sensing technology.

Additional advantages and novel features of the new sensor fish and methods will be set forth as follows and will be readily apparent from the descriptions and demonstrations set forth herein. Accordingly, the following descriptions of the present fish and methods should be seen as illustrative of the fish and methods and not as limiting in any way.

SUMMARY

Pacific Northwest National Laboratory has completed a two-year project to develop a "sensor fish" that addresses the limitations of the prior art devices. The result and improved or GEN 2 sensor fish provides improved robustness of the design and enhanced measurement capabilities using innovative sensors and circuitry; reduced future costs and a model that is capable of deployment in numerous areas wherein such items were not previously deployable. This sensor fish contains sensors for acceleration, rotation, magnetic field intensity, pressure, and temperature. A low-power microcontroller collects data from the sensors and stores up to 5 minutes of data on a non-volatile flash memory. A rechargeable battery supplies power to the sensor fish. A recovery system helps locating sensor fish. The package, when ready for use is nearly neutrally buoyant and thus mimics the behavior of an actual fish.

To operate the sensor fish, the user activates the microcontroller using a magnet, and then drops the device in the water (typically, on the upstream side of a dam). The microcontroller waits for a preselected and preprogrammed period of time and then samples data from each sensor at up to 8,092 Hz. Data collection continues for a preselected programmable period of time configurable time, or until the internal memory is full. The microcontroller then activates the recovery mechanism on each end of the enclosure to release weights for ballast causing the fish to rise to the surface and provide a sensing alarm (e.g. radio frequency transmission and strobe lights) to facilitate the identification and location of the device. The recovery mechanism consists of a spring-loaded weight tied down with a piece of fishing line that loops over a nichrome wire. The microcontroller briefly applies a large current through the nichrome wire, which heats up the wire, severs the fishing line, and releases the weight on each end. The weights drop and the package rises to the surface. The microcontroller then activates integrated LED flashers along with a radio frequency (RF) beacon so users can locate the package. Applying the magnet again turns off the beacons. After collection, from the water, the sensor fish is then configured for placement into a docking station where in the data collected during the event can be down loaded into a larger system for analysis. The docking station plugs into the flex circuit board on one end to recharge the battery and download the sensor data. After the data is downloaded the flash memory is then typically erased. New weights and fishing line (connectors) are installed and the sensor fish is ready for the next deployment.

The purpose of the foregoing summary is to assist the United States Patent and Trademark Office and the general public, especially the scientists, engineers, and practitioners in the art who are not familiar with patent or legal terms or phraseology, to determine quickly from a cursory inspection the nature and essence of the technical disclosure of the application. This summary can be relied upon to support the claimed invention; however the summary is not intended to be limiting as to the scope of the claims in any way.

Various advantages and novel features of the present disclosure are described herein and will become further readily apparent to those skilled in this art from the following detailed description. In the preceding and following descriptions only the preferred embodiments of the invention are shown and described, by way of illustration of the best mode contemplated for carrying out the invention. As will be realized, the invention is capable of modification in various respects without departing from the invention. Accordingly, the drawings and description of the preferred embodiment set forth hereafter are to be regarded as illustrative in nature, and not as restrictive.

DESCRIPTION

Figure 1A:
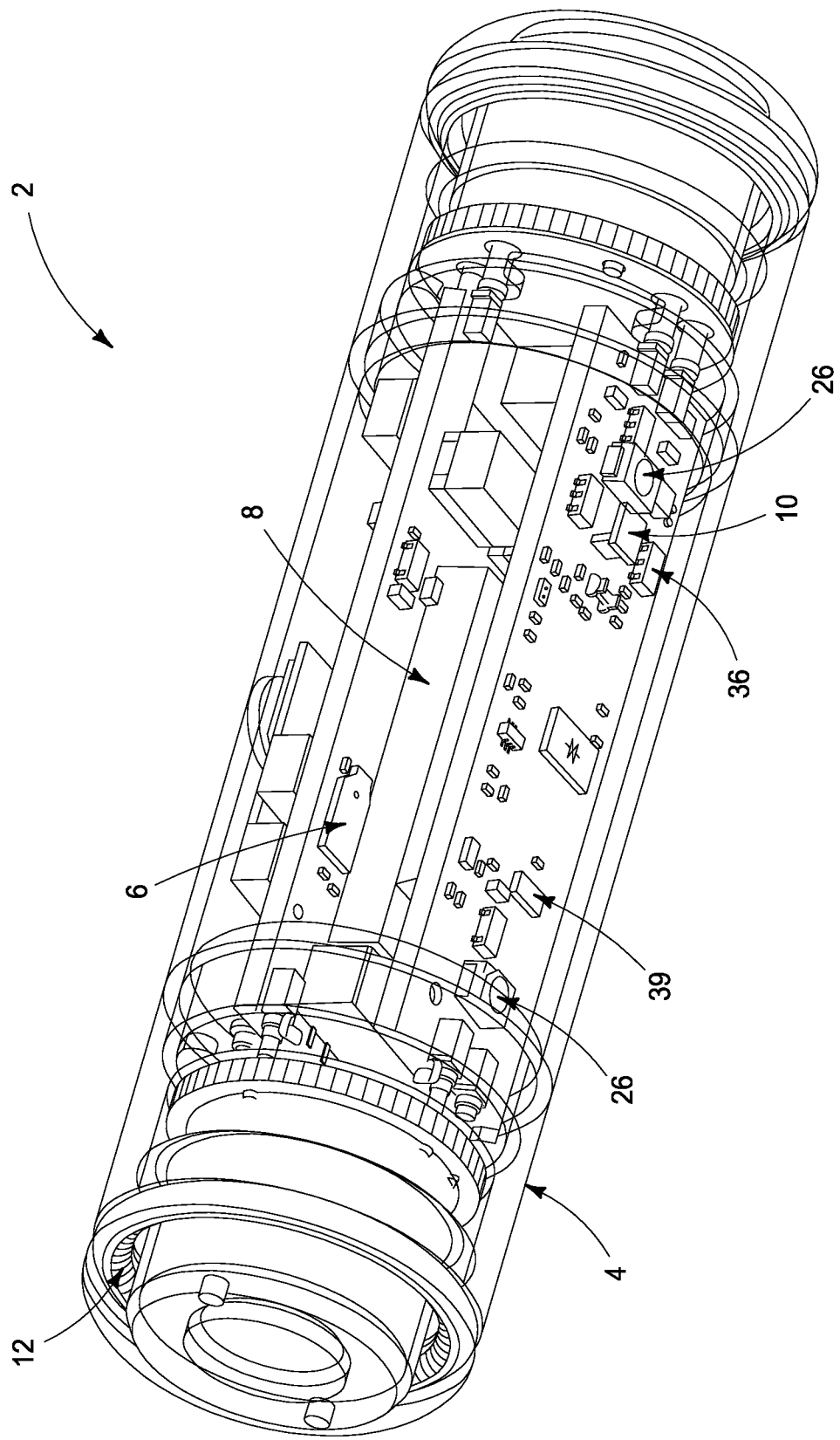
FIGS. 1A and 1B are perspective side views of a first preferred embodiment of the present invention
Figure 1B:
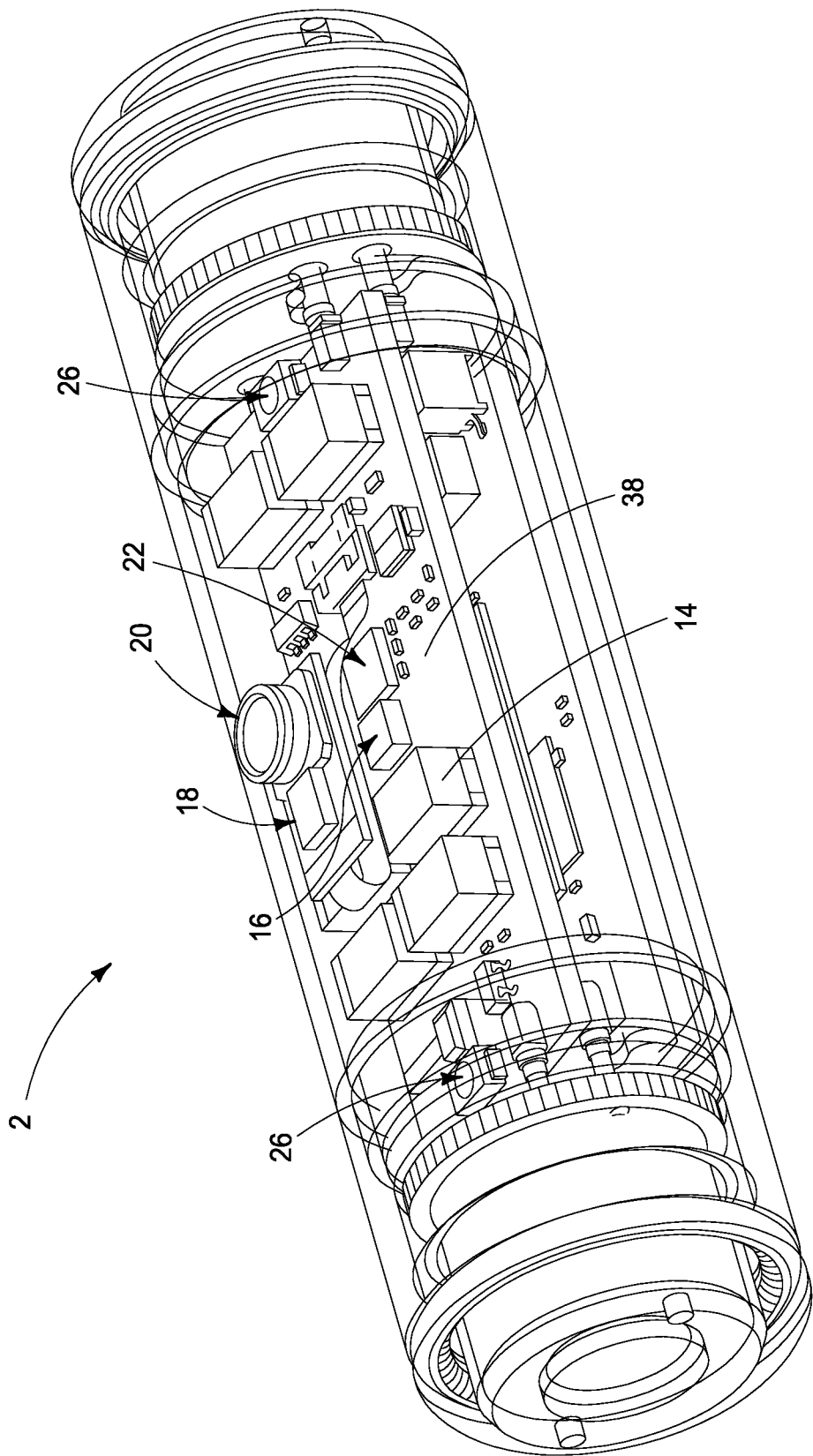

This disclosure is submitted in furtherance of the constitutional purposes of the U.S. Patent Laws "to promote the progress of science and useful arts" (Article 1, Section 8). The following description includes the preferred best mode of one embodiment of the present invention. It will be clear from this disclosure that the invention is not limited to these illustrated embodiments but that the invention also includes a variety of modifications and embodiments thereto. Therefore the present description should be seen as illustrative and not limiting. While the invention is susceptible of various modifications and alternative constructions, it should be understood, that there is no intention to limit the invention to the specific form disclosed, but, on the contrary, the invention is to cover all modifications, alternative constructions, and equivalents falling within the spirit and scope of the invention as defined in the claims.

FIGS. 1-5 show a variety of embodiments of the present invention. Referring first to FIGS. 1A and 1B, views of one embodiment of the present invention are shown. FIGS. 1A and 1B show a "sensor fish" 2 having a housing 4 that defines a body. The housing 4 is dimensioned to have the size and density similar to those of a yearly salmon smolt typically averaging 3 to 5.25 inches (73-134 mm). In this embodiment the housing 4 is a clear polycarbonate cylinder 24.5 mm in diameter and 89.9 mm long, weighs approximately 42.1 g, when loaded with the sensors (26, 18, 20, 22, and recovery mechanisms 24 and has a size and density similar to those of a yearling salmon smolt. This body 4 contains three-dimensional (3D) rotation sensors (i.e. 3-axis gyroscope) 22, 3D linear acceleration sensors (i.e. 3-axis accelerometers) 16, a pressure sensor 20, a temperature sensor 18, a 3D orientation sensor (i.e. 3-axis magnetometer) 6, a radio-frequency (RF) transmitter 10, a recovery mechanism 24, and a communication module. A low-power microcontroller 6 collects data from the sensors and stores up to 5 minutes of data on an internal non-volatile flash memory at a sampling frequency of 2,048 Hz (can be configured to up to 8,192 Hz). A rechargeable battery 8 supplies power to the sensor fish. A recovery mechanism 24 makes the sensor fish positively buoyant and float to the surface for recovery after a pre-programmed time. For ease of use the housing was made of a clear durable poly carbonate material. However in other applications appropriate modifications could also be made to this particular design.

The primary components were placed so that the center-of-gravity is very close to the geometric center of the housing 4. While these particular components are described below, in additional detail it is to be distinctly understood that the invention is not limited thereto but may be variously alternatively configured within the scope of the invention as defined by the claims. In the described embodiment, the primary accelerometer 16 (ADXL377, Analog Devices, Inc., Norwood, Mass., USA) is a chip-scale package, low power, three-axis analog component with a typical full-scale range of ±200 g per axis and a 10,000 g shock survival overload rating. The accelerometer 16 also has user-selectable bandwidths to suit different applications, with a range of 0.5 Hz to 1300 Hz for the x-axis and y-axis (see FIGS. 1A and 1B for axis definition) and a range of 0.5 Hz to 1000 Hz for the z-axis. It is placed at the center of a flex circuit board 36, which coincides with the center of mass of the device, for the greatest accuracy.

The gyroscope 22 (ITG-3200, InvenSense, Inc., San Jose, Calif., USA) is a digital-output three-axis microelectromechanical systems component with a full-scale range of ±2000°/s per axis. The ITG-3200 includes three 16-bit analog-to-digital converters, which are used to digitize the gyroscope outputs. It includes a user-selectable internal low-pass filter bandwidth and an inter-integrated circuit ($I^2C$) interface. The initial zero-rate output is ±40°/s, and the linear acceleration sensitivity is 0.1°/s·g. The gyroscope 22 also includes an embedded temperature sensor 18. The gyroscope 22 is mounted near the center of the flex circuit board 36, close to the accelerometer 16.

The eCompass module (LSM303D, STMicroelectronics, Geneva, Switzerland) integrates a three-axis digital accelerometer 16 and a three-axis digital magnetometer 6 in the same package. The accelerometer 16 has a maximum full-scale range of up to ±16 g, and thus is not suitable for collecting data during the most intense part of the passage (e.g., collision with structures), but it can improve the precision of the remaining data. The magnetometer 6 has a selectable full-scale range of up to ±12 gauss. As with the gyroscope 22, this component supports an I²C serial bus interface and has an on-board temperature sensor 18.

The pressure sensor 20 (M55412-BM, Measurement Specialties, Inc., Hampton, Va., USA) on the flexible board consists of a micromachined silicon pressure sensor 20 die mounted on a 6.2×6.4 mm ceramic carrier; it has a full-scale range of 14 bar (203 psia) with a linear range of 12 bar (174 psia). The overpressure rating is 30 bar (435 psia). The pressure sensor is of the Wheatstone bridge type with a typical full-scale span of 150 mV and zero offset of ±40 mV. The positive and negative outputs connect to an instrumentation amplifier on the flex circuit board 36. This amplifier has gain set to 12.9 and offset set to 50 mV, which allows an input range of −40 to +190 mV for 0 to 12 bar measurements.

The primary temperature sensor 18 (TC1046, Microchip Technology Inc., Chandler, Ariz., USA) on the flexible board is also an analog component with linear temperature slope of 6.25 mV/° C. and a full-scale range of −40 to +125° C.

The temperature sensor is mounted close to the pressure sensor 20, with the intervening space covered with heat-conductive epoxy (Omega Bond 200, OMEGA Engineering) to improve the thermal contact between the temperature sensor 18 and the metal enclosure of the pressure sensor 20, which comes into direct contact with the water.

Figure 3A:
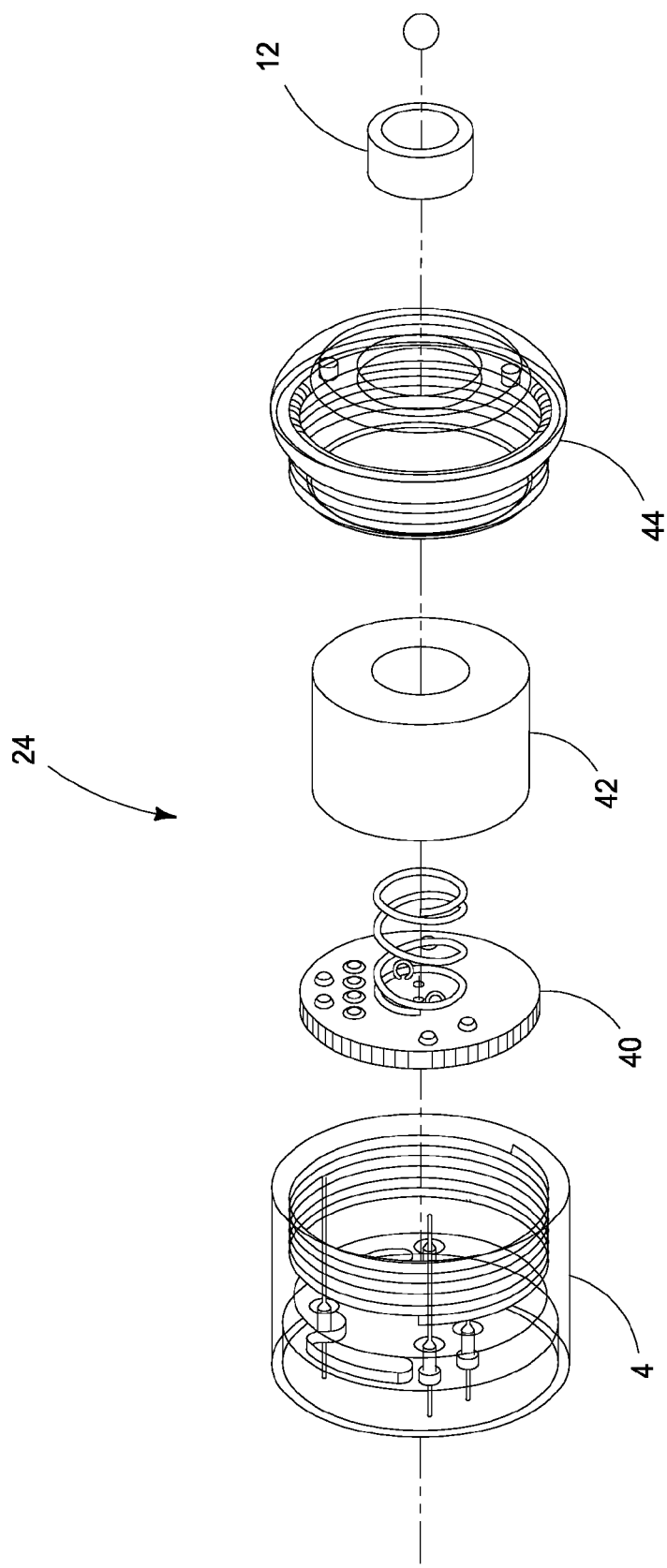
FIGS. 3A and 3B are detailed views of the recovery mechanism of the present invention.
Figure 3B:
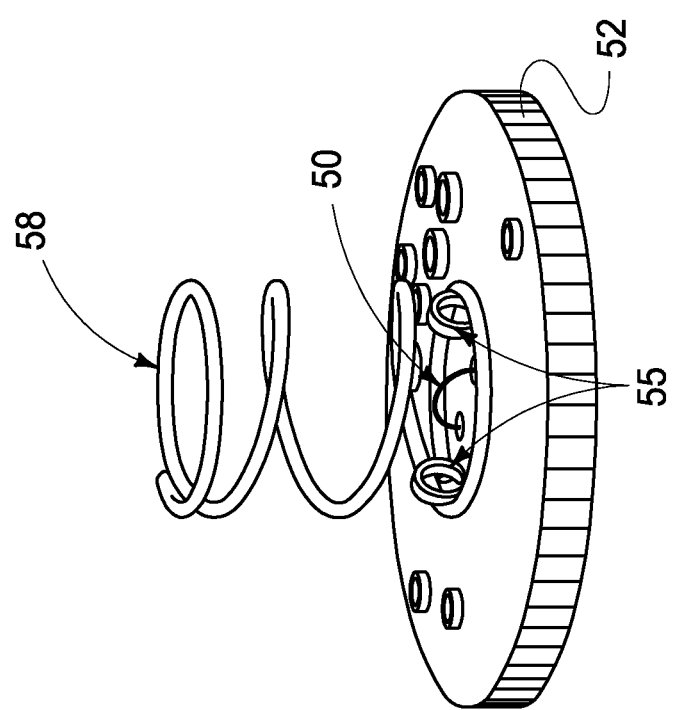

Referring to FIGS. 3A and 3B, recovery mechanism 24 is depicted that includes a download board and a program board 40, each located at one end of the sensor fish. The download board 40 allows users to download serial data from the sensor fish and recharge the battery, and the program board allows users to update the microcontroller firmware. Both boards contain a nichrome wire 50 used for the recovery mechanism, which consists of a spring-loaded 58 weight 12 tied down with a piece of fishing line that connects to an end cap 52 and loops 55 over the nichrome wire 50. A foam insert 42 can be used to provide increased buoyancy to the unit. In use the microcontroller 14 briefly applies a large current to the nichrome wire 50, which heats up the wire 50, severs the fishing line 48, and releases the weight 12 on the end. The process is then repeated for the opposite end of the sensor fish 2 to release a second weight 12. Without the weights the sensor fish 2 rises to the surface. This typically begins after the first weight has been released. A radio-frequency transmitter 10 and four high-intensity orange light-emitting diodes (LEDs) 26 are activated periodically so that users can locate the device. The carrier frequency of the RF pulse is between 164 to 166 MHz for compatibility with existing receiver equipment. However, the frequency can also be set between 1MHz to 220MHz to accommodate different receiver equipment. The LEDs 26 face outward to permit good visibility in most orientations, and the color was chosen to provide good contrast with water. For scenarios where an orange LED is not suitable other sensor fish can be manufactured using an alternate color.

The users activate the sensor fish 2 by holding a magnet near a magnetic switch 39 located on the main flex circuit board 36. The sensor fish 2 then performs a self-check to make sure that the battery voltage is above a preset threshold and the flash memory is empty. A successful check causes the status LED 26 to flash yellow indicating the start of a configurable data acquisition delay time; otherwise, the status LED flashes red. After the delay time has elapsed, the sensor fish 2 starts collecting sensor data and saving it to flash memory. Once data acquisition is complete, the status LED 26 first flashes green indicating the start of a configurable resurface time. After the resurface time has elapsed the sensor fish 2 activates the recovery mechanism 24. Finally, the LEDs and RF transmitter are activated periodically until the sensor fish 2 is located and the magnetic switch 39 is triggered. After data is collected and the sensor fish 2 is retrieved, it is placed into the docking station. The status LED 26 on the sensor fish 2 is set to red, and if/when the battery is fully charged, the battery charging indication LED 26 is set to green, otherwise, LED 26 is set to red. The sensor fish 2 then waits for serial commands from the docking station sent by the sensor fish Communicator software. The docking station plugs into the sensor fish 2 on the download board 26 to recharge the battery 8 and download the sensor data via a two-pin serial interface. The docking station uses a transistor-transistor-logic to Universal Serial Bus (TTL-to-USB) converter module to transfer the data to a personal computer. It can service up to four sensor fish 2 simultaneously. Users interact with the sensor fish via communication software developed at Pacific Northwest National Laboratory (PNNL), with the serial port configured to 921.6 kHz, 8 data bits, 1 start bit, 1 stop bit, and no parity. The sensor fish communicator can also be used to convert the raw binary data file into a comma-separated value (CSV) file with physical units, using calibration coefficients, and plot the resulting data. All of the sensors, including the pressure sensor 20, three-axis accelerometer 16, three-axis gyroscope 22, three-axis magnetometer 6, and temperature sensor 18 were calibrated and evaluated individually before and after assembly in the lab. All data analysis was conducted using MATLAB programs (The MathWorks, Inc., Natick, Mass., USA).

Figure 2:
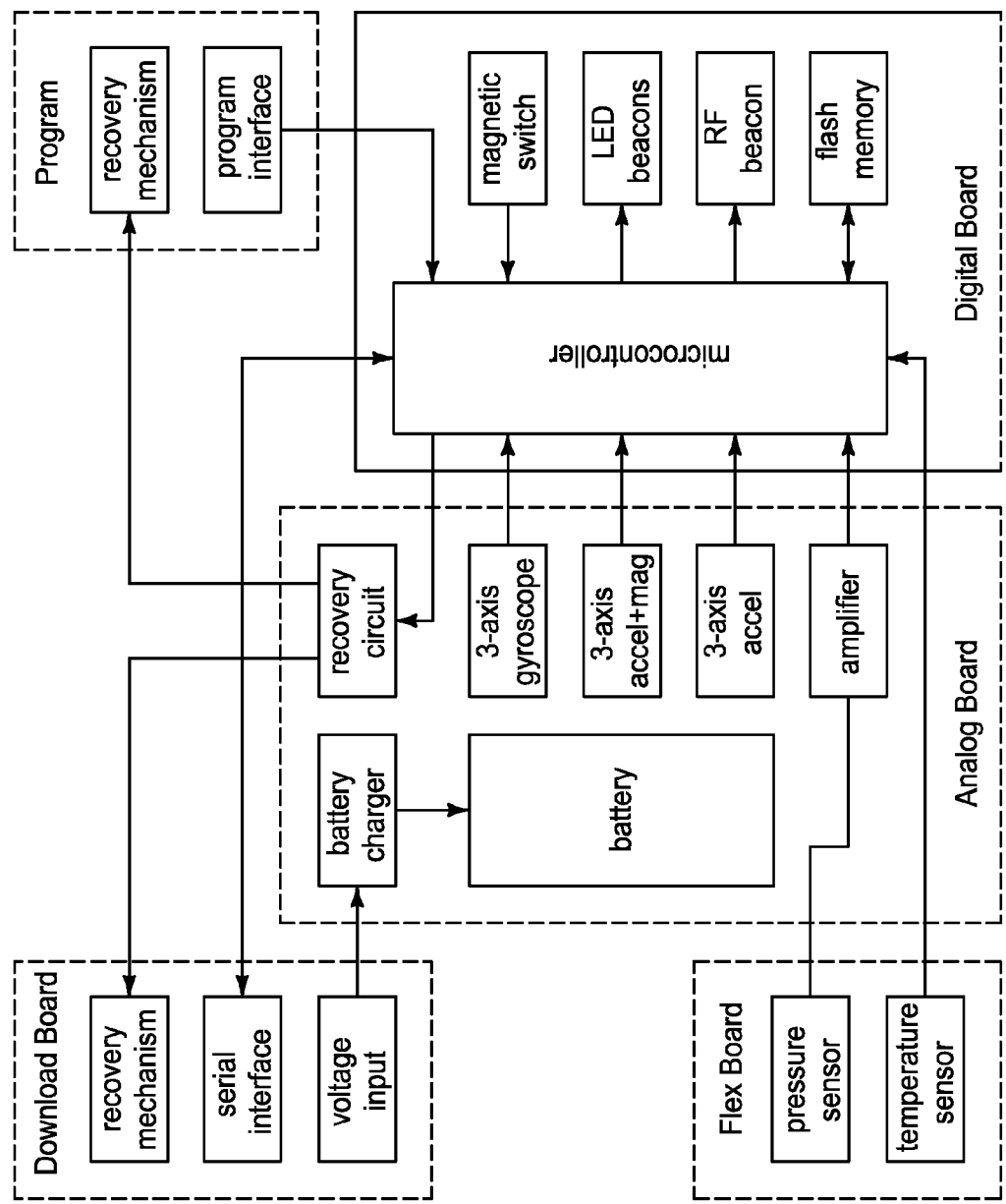
FIG. 2 is a block diagram of the electrically connected components of the present invention.

The electronics design of the new sensor fish 2 is shown in an overall block diagram in FIG. 2. The design contains two main circuit boards: an analog board for most of the sensors, and a digital board for the microcontroller 14 and various peripherals. These two boards are stacked on top of each other, with the battery 8 in between, and mounted in the main body 4 of the device. Additional sensors are mounted onto a flexible circuit board 36 and glued into a port on the outer enclosure. A small adapter board on one end of the sensor fish 2 contains a recovery mechanism 24, serial download interface, and input to the battery charger. This board connects to a docking station, not shown. Another adapter board on the opposite end of the device contains a second recovery mechanism and a port for reprogramming the microcontroller 14.

Power to the device is provided by a battery 8. In the preferred embodiment the battery 8 is a lithium polymer battery 8 with a nominal capacity of 100 mA·h. The maximum recommended discharge current is 200 mA, and the recommended recharge current is 50 mA. An integrated protection circuit cuts off the battery on an over-discharge condition. In one embodiment the maximum continuous current consumption of the sensor fish 2 is about 70 mA when the flash memory is being erased. However, this operation is normally performed in the docking station with the battery charger supplying extra current. The maximum transient current consumption is about 130 mA with the LED flashers 26 on. The battery 8 connects to the board at terminals TP1 and TP2. The positive battery terminal is not exposed outside the sensor fish 2 to prevent accidental short circuits or current leakage while in water. The battery charger U5 can accept up to 6.0 V, and has an output current limit set to 50 mA. The LDO regulator U6 with active high enable generates a 3.0 V supply for all the sensors.

The primary accelerometer 16 is a 3-axis analog component with a typical full-scale range of ±200 g. A 4.7 nF capacitor on the outputs sets the bandwidth of the accelerometers to 1 kHz. The outputs then drive the analog inputs of the microcontroller 14. As the microcontroller 14 oversamples the accelerometer 16 at 8.192 kHz, additional anti-aliasing filters proved unnecessary. The accelerometer 16 is located at the center of the flex circuit board 36 for greatest accuracy. Other analog sensors are mounted on the flex circuit board 36. The pressure sensor 20 is an analog component with a full-scale range of 14 bar (203 psia) with a linear range of 12 bar (174 psia). The overpressure rating is 30 bar, or 435 psia. A similar component is available with a full-scale range of 70 bar and overpressure rating of 180 bar, but lower linearity. The pressure sensor 20 is of the Wheatstone bridge type with a typical full scale span of 150 mV and zero offset of ±40 mV. The positive and negative outputs connect to instrumentation amplifier on the analog board. This amplifier has gain set to 12.9 and offset set to 50 mV, which allows an input range of −40 to +190 mV.

The temperature sensor 18 on the flex circuit board is also an analog component with a full-scale range of −40 to +125° C. As a high bandwidth is not required, the output connects directly to the microcontroller 14 on the digital board. The temperature sensor 18 is mounted close to the pressure sensor 20, with the intervening space covered with heat-conductive epoxy to improve the thermal contact between the temperature sensor 18 and metal enclosure of the pressure sensor 20, which comes in close proximity to the water. The gyroscope 22 is a 3-axis digital component with a full-scale range of ±2000°/s. The initial zero-rate output is ±40°/s, and the linear acceleration sensitivity is 0.1°/s·g. The gyroscope 22 also includes a temperature sensor 18. The digital I2C interface uses a separate power supply to mitigate noise. The gyroscope 22 is mounted near the center of the flex circuit board 36, close to the accelerometer 16. The 3-axis digital accelerometer 16 and 3-axis digital magnetometer 6 are combined into the same package. The accelerometer 16 has a maximum full-scale range of up to ±16 g, and thus is not suitable for collecting data during the most intense part of the passage, but can improve the precision of the remaining data. The magnetometer 6 has a maximum full-scale range of up to ±12 gauss. As with the gyroscope 22, the component has an on-board temperature sensor 18 and uses a separate power supply for the digital I2C interface. The mounting location is near one corner of the flex circuit board 36, as alignment with the center of mass is not critical. The controller circuitry for the recovery mechanism is placed on the analog board due to space constraints. Noise from this component is not a concern since the data collection ends before the device resurfaces. Controller first charges a capacitor bank to −30 V. Bleeder resistors and help equalize the voltages across the series tantalum capacitors. The energy is then directed through the nichrome wires 50 via transistors. The other ends of the nichrome wires 50 are tied to ground. The resulting large current spike immediately severs the fishing line. Note that the −30 V signal is not exposed to the environment to prevent a leakage current path through the water. The battery power and sensor data enters the digital board via headers. A low quiescent current LDO regulator generates a 3.0 V supply for the microcontroller 14, and is always active while the battery 8 is connected. A separate LDO regulator with active high enable provides another 3.0 V supply for the flash memory.

A 16-bit PIC microcontroller 14 that operates the sensor fish 2. When not collecting data, the microcontroller 14 operates from an internal low-frequency oscillator to save power. The LDO regulators for the sensors and flash memory are turned off. The user activates the sensor fish by holding a magnet near magnetic switch 39. The digital output of this Hall Effect sensor drives an interrupt pin of the microcontroller 14. The microcontroller 14 then turns on the LDO regulators and activates crystal to generate a 14.7456 MHz clock. This frequency is an even multiple of the standard 921.6 kHz baud rate used for downloading data. Bi-color LED 1 blinks green, yellow, or red to indicate the system status. The microcontroller 14 contains a 12-bit successive approximation analog-to-digital converter (ADC) to digitize the sensor data. The sensor supply voltage and ground from the analog board connect to the ADC voltage reference pins 19 and 20. This configuration reduces the effect of digital noise. Note that the ADC supply pins must be connected to the main supply pins 39 and 40; in fact, a low-resistance path exists between the two supplies inside the microcontroller 14. Besides the sensor data, the microcontroller 14 also measures the battery voltage via transistor and the associated resistor divider. In this particular embodiment the flash memory has a capacity of 16 MB, although a pin-compatible 32 MB replacement is available. The memory is organized into pages of 256 B; writing a full page at a time is most efficient. The microcontroller 14 communicates with the flash memory via SPI.

Transistors, of the analog board for example, can be used to activate the recovery mechanism 24. The gate-source voltage on these transistors steps from 0 to about 10 V. After the sensor fish 2 resurfaces, the microcontroller 14 blinks four high-intensity orange LEDs 26 to that users can locate the device. The color was chosen to provide good contrast with water. The LEDs 26 face outward to permit good visibility in most orientations. The microcontroller 14 also activates an integrated RF beacon upon resurfacing which generates the carrier signal, and drives the antenna. The microcontroller 14 simply turns on and off to generate an RF pulse with transistor. The carrier frequency is between 164 to 166 MHz for compatibility with existing receiver equipment. The frequency can also be set between 1 MHz to 220 MHz to accommodate different receiver equipment when using different components. The antenna may be folded inside the housing or fed through the outer enclosure to form a "tail". While the present embodiment is shown, it is to be understood that various other alternative embodiments are contemplated within the scope of the claims of the present application.

The analog and digital boards plug into two adapter boards, one located at each end of the sensor fish 2, which contain the nichrome wire 50 used for the recovery mechanism. One board, known as the download board, allows users to download serial data from the sensor fish 2 and recharge the battery 8. The other board, known as the program board, allows users to update the microcontroller firmware. The docking station charges the battery via power and ground connections on the download board, and downloads data from the microcontroller via a two-pin serial interface. The data transfer uses RS-232 at 921.6 kHz baud rate, but with 3.0 V logic levels. The docking station may use a commercial TTL-to-USB converter cable or similar circuitry to pass the data to a personal computer. When the sensor fish 2 is placed in the docking station, the RX signal is pulled high and wakes the microcontroller from sleep mode. Note that the RX signal is connected to two pins on the microcontroller: one for the serial communication, and the other for the dedicated interrupt. The analog board, digital board, download board, and flex board are combined on the same panel to reduce fabrication costs. Each is a four-layer board in this application. The microcontroller contains firmware which provides the logic for operating the sensor fish 2, whereas the other modules define the interfaces to various components with the necessary initialization routines. Short functions are implemented as macros to reduce the execution time. Preferably the full version of the MPLAB C30 compiler is required to generate optimized code; otherwise, the sensor fish 2 will work, but the sampling rate may not be consistent.

Upon reset, the microcontroller 14 calls Port_Initialize to set initial values of all output pins. Parameters such as the data collection time are set to default values. The startup clock source is the internal 32.768 kHz oscillator. Execution then falls into Port_Wait, which places the microcontroller 14 in sleep mode until an interrupt occurs. As described earlier, the two interrupt sources are the magnetic switch and the RX signal from the docking station. If the docking station pulls the RX signal high, the microcontroller 14 enters the main_download function. The status LED is set to red, the flash memory is powered on, and the external 14.7456 MHz crystal is activated. The function then waits for serial commands from the docking station. A complete listing of commands appears later in this section. The Uart_Update function is responsible for processing the serial command string and decoding the associated parameter value, if any. Any invalid characters cause the serial interface to be reset. The microcontroller 14 only exits main_download if the docking station sends a quit ("Q") command and the RX signal then falls back low.

If the magnetic switch trips, the microcontroller calls main_check to ensure that the battery voltage is over a preset threshold and the flash memory is empty. A successful check causes the status LED to flash yellow for a configurable delay time; otherwise, the status LED flashes red and the microcontroller returns to the main loop. After the delay time has elapsed, the microcontroller 14 calls main_acquire to collect sensor data. The sensors, flash memory, and 14.7456 MHz crystal are all powered on and initialized. The function then executes a time-critical loop to sample the sensor data. The loop consists of 24 data acquisition steps, or ticks. The time interval between each tick is metered by Timer2, which fires at 24.576 kHz intervals. Thus, the 24 ticks repeat at an overall rate of 1.024 kHz. However, some sensors are sampled more than once: the analog sensors at 8.192 kHz, the gyroscope at 2.048 kHz, and the magnetometer at 1.024 kHz. The microcontroller adds four analog samples together and saves the data at 2.048 kHz. This process, known as oversampling, reduces noise and preserves the full bandwidth of 1.024 kHz.

Table 1 lists the operations performed during each tick. The ADC and two I2C modules operate in parallel, so the microcontroller generally starts the operations and then reads the results at the beginning of the next tick. However, two ADC conversions are performed for each tick.

TABLE 1

Operations performed in data acquisition function.

| Tick | ADC | I2C to gyroscope | I2C to magnetometer |
|---|---|---|---|
| 0 | accel x + pressure | start + address + write | start + address + write |
| 1 | accel y + temperature | command | command |
| 2 | accel z + voltage | start + address + read | start + address + read |
| 3 | accel x + pressure | gyro t upper byte | mag t upper byte |
| 4 | accel y + temperature | gyro t lower byte | mag t lower byte |
| 5 | accel z + voltage | gyro x upper byte | stop + start + address + write |
| 6 | accel x + pressure | gyro x lower byte | command |
| 7 | accel y + temperature | gyro y upper byte | start + address + read |
| 8 | accel z + voltage | gyro y lower byte | mag x upper byte |
| 9 | accel x + pressure | gyro z upper byte | mag x lower byte |
| 10 | accel y + temperature | gyro z lower byte | mag y upper byte |
| 11 | accel z + voltage | stop | mag y lower byte |
| 12 | accel x + pressure | start + address + write | mag z upper byte |
| 13 | accel y + temperature | command | mag z lower byte |
| 14 | accel z + voltage | start + address + read | stop + start + address + write |
| 15 | accel x + pressure | gyro t upper byte | command |
| 16 | accel y + temperature | gyro t lower byte | start + address + read |
| 17 | accel z + voltage | gyro x upper byte | accel x upper byte |
| 18 | accel x + pressure | gyro x lower byte | accel x lower byte |
| 19 | accel y + temperature | gyro y upper byte | accel y upper byte |
| 20 | accel z + voltage | gyro y lower byte | accel y lower byte |
| 21 | accel x + pressure | gyro z upper byte | accel z upper byte |
| 22 | accel y + temperature | gyro z lower byte | accel z lower byte |
| 23 | accel z + voltage | stop | stop |

The main_acquire function writes sensor data to the flash module during ticks 11 and 23. This module contains an internal buffer for temporary data storage. The function then calls Flash_Update periodically to transfer words from the internal buffer to the flash memory. After 256 B are transferred, Flash_Update sends a page program command to write the data into nonvolatile storage. Subsequent data values are placed in the buffer until the flash memory is ready. Flash_Update is designed to complete quickly in the spare cycles available between each tick. Once data acquisition is complete, the microcontroller returns to low-power mode and calls main_resurface. The status LED first flashes green for a configurable delay time. The function then activates the boost converter and engages the recovery mechanisms, one at a time. Finally, the LED and RF beacons are activated periodically until the sensor fish 2 is located and the magnetic switch is tripped. The sensor fish 2 saves data in binary format as a series of records. One record is created for each loop of 24 ticks in the data acquisition function, which occurs every 1,024 Hz. The record consists of a 2-byte header, set to 8000 hex, followed by the sensor data as 2-byte words. All values are in big-endian format with the upper byte first. No data values are 8000 hex, permitting records to be synchronized easily. Each record contains two values from the analog sensors and gyroscope, as these sensors are saved at 2,048 Hz, and one value from the magnetometer and secondary accelerometer, as these sensors are saved at 1,024 Hz. The microcontroller 14 outputs the binary data as described in response to a "B" command. For the "T" command, the microcontroller 14 converts each 2-byte word to a signed integer and outputs the values as space-delimited text. The header of 8000 hex is converted into a newline to delimit consecutive data records. The sensor fish communicator software enables communication between the flash memory and a computer for performing the data analysis. See Table 2 for example data format.

TABLE 2

Format of one Sensor Fish data record.

| Item | Bytes |
| --- | --- |
| header (8000 hex) | 2 |
| primary accelerometer x, y, z | 6 |
| pressure | 2 |
| temperature | 2 |
| battery voltage | 2 |
| gyroscope temperature | 2 |
| gyroscope x, y, z | 6 |
| primary accelerometer x, y, z | 6 |
| pressure | 2 |
| temperature | 2 |
| battery voltage | 2 |
| gyroscope temperature | 2 |
| gyroscope x, y, z | 6 |
| magnetometer temperature | 2 |
| magnetometer x, y, z | 6 |
| secondary accelerometer x, y, z | 6 |
| TOTAL | 56 |

Figure 4:
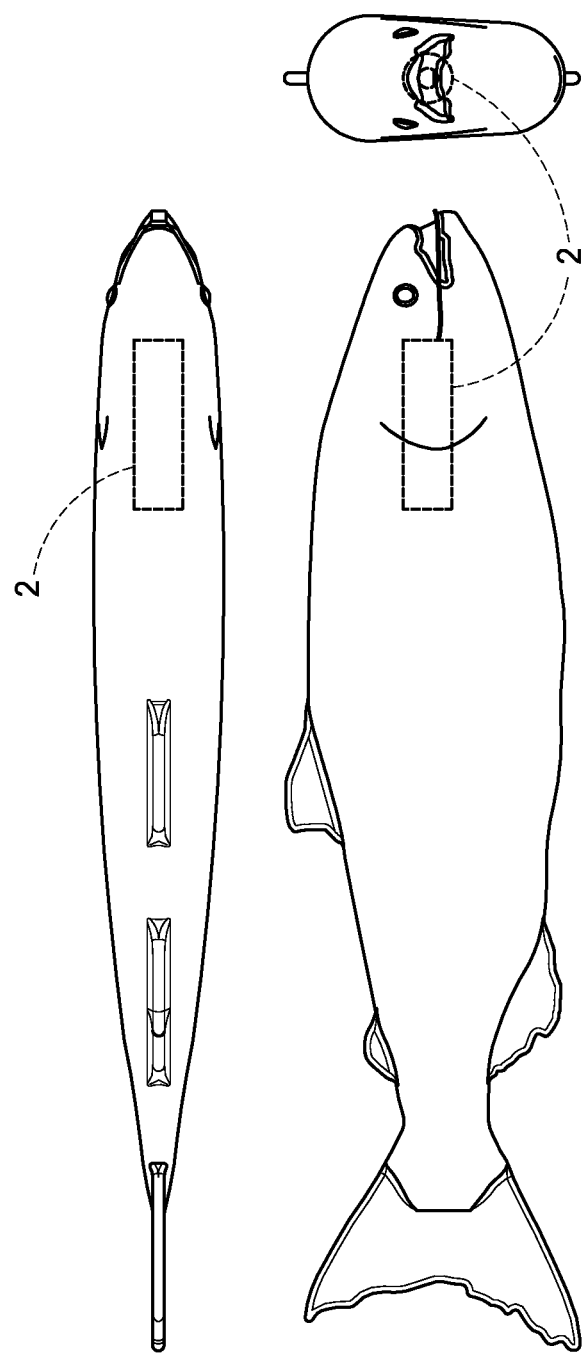
FIG. 4 is a perspective view of another embodiment of the deployment of the present invention.
Figure 5:
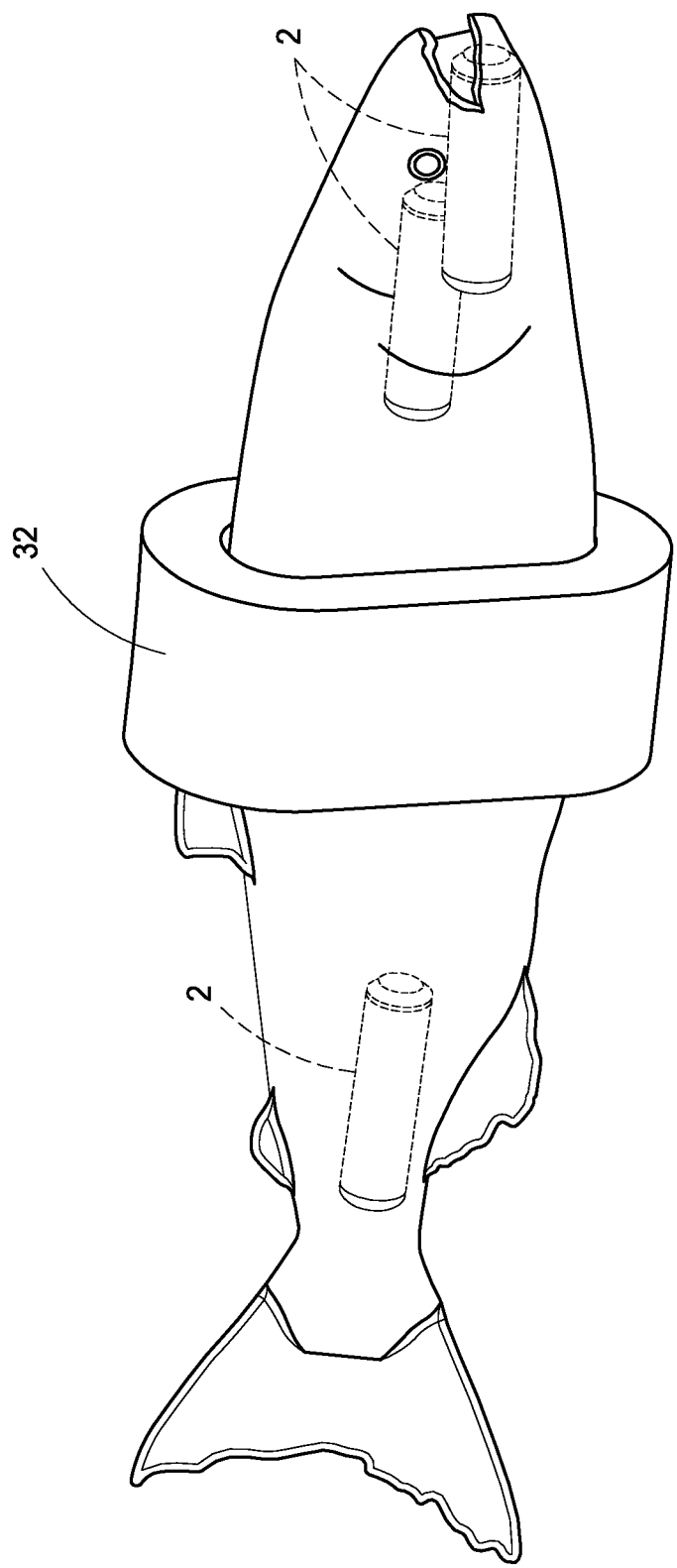
FIG. 5 is a perspective view of another embodiment of the present invention.

In some embodiments the senor fish of the present design (termed Adults Senor Fish) can be combined within a larger body to provide separate sensing for portions of a fish and to obtain data of the particular environmental conditions and stresses that would be placed upon a larger fish passing through such an environment. An example of such an embodiment is shown in FIGS. 4-5 As shown in FIGS. 4-5 placement of the various sensors within a larger fish carcass (a simulated fish shaped body made of resilient resin) that floats within the water and mimics the movement of a fish as it moves through the hydraulic system. The recovery system and weights for recovery are not always applied in these large body embodiments. In some deployments the fish were collected into a pool and netted.

Adult sensor fish was applied to understand the physical conditions adult fish experience when they pass through the Whoosh Transport Conduits. The Whoosh system is an innovative adult fish passage method. Two different lengths of Whoosh Transport Conduits (40 and 250 ft) were set up for the evaluation. The adult sensor fish successfully collected physical conditions data through both configurations.

A field evaluation of the new sensor fish was performed at the spillway of Ice Harbor Dam, which is located on the Snake River, 16 river kilometers from its confluence with the main stem of the Columbia River, in south-central Washington State. The dam is 860 m long and 30.5 m tall and consists of a six-unit powerhouse, a ten-bay spillway, a navigation lock, two fish ladders, a juvenile fish bypass facility, and a removable spillway weir. The spillway is 180 m long and has 15.2 m tainter gates. Three sensor fish were released in front of Spillbay 6. During the releases, the flow from Spillbay 6 was 8.5 kcfs (241 m$^3$/s) and the total spill was 41.6 kcfs (1,178 m$^3$/s). The sensor fish were introduced into the spill discharge flow from the spillway deck using a fishing pole and a downrigger release clip (Black Marine RC-95 downrigger release clip) at a depth of approximately 15.2 m immediately upstream of the spill opening. The sensor fish were recovered in the tailrace and data was successfully recovered from all sensors for all releases.

While various preferred embodiments of the invention are shown and described, it is to be distinctly understood that this invention is not limited thereto but may be variously embodied to practice within the scope of the following claims. From the foregoing description, it will be apparent that various changes may be made without departing from the spirit and scope of the invention as defined by the following claims.

What is claimed is:

1. A sensor fish that collects data related to the environmental conditions experienced by fish while passing through hydraulic systems such as hydro-electric power dams, said sensor fish comprising:
a housing defining a body;
at least one component sensor configured to detect at least one parameter selected from the group consisting of orientation, acceleration, rotational velocity, magnetic field intensity, pressure, and external temperature;
a controller located within said housing that collects data from the sensors and stores said data in memory;
a battery located within said housing that supplies power to the sensors and microcontroller within the sensor fish; and
a recovery system operably connected to said housing and said microcontroller that when actuated by said microcontroller causes said sensor fish to float upward and sends a signal for recovery of the sensor fish, wherein the recovery system includes a spring-loaded weight coupled to fishing line looped over a nichrome wire, that when heated under the control of the microcontroller, severs the fishing line, and releases the weight on each end causing the sensor fish to float upward.

2. The sensor fish of claim 1 wherein the housing contains at least two sensors; each sensor configured to detect at least one parameter selected from the group consisting of orientation, acceleration, rotational velocity, magnetic field intensity, pressure, and external temperature.

3. The sensor fish of claim 1 where in the housing further contains at least three sensors; each sensor configured to detect at least one parameter selected from the group consisting of orientation, acceleration, rotational velocity, magnetic field intensity, pressure, and external temperature.

4. The sensor fish of claim 1 where in the housing further contains at least four sensors; each sensor configured to detect at least one parameter selected from the group consisting of orientation, acceleration, rotational velocity, pressure, and external temperature.

5. The sensor fish of claim 1 where in the housing further contains at least five sensors; each sensor configured to detect at least one parameter selected from the group consisting of orientation, acceleration, rotation, magnetic field intensity, pressure, and external temperature.

6. The sensor fish of claim 1 where in the housing further contains at least six sensors; each sensor configured to detect at least one parameter selected from the group consisting of orientation, acceleration, rotation, magnetic field intensity, pressure, and external temperature.

7. The sensor fish of claim 1 wherein the housing when ready for use is nearly neutrally buoyant.

8. The senor fish of claim 1 wherein the microcontroller is configured to wait for a preselected and preprogrammed period of time and then sample data from each sensor at up to 8,192 Hz for a preselected programmable period of time.

9. The sensor fish of claim 1 wherein the recovery mechanism includes a sensing alarm to facilitate the identification and location of the device.

10. The sensor fish of claim 1 wherein the recovery mechanism includes LED.

11. The sensor fish of claim 1 wherein the recovery mechanism includes a radio frequency (RF) beacon.

12. The senor fish of claim 1 wherein said microcontroller is configured to be selectively activated and deactivated by a magnetic field.

13. The sensor fish of claim 1 wherein said microcontroller is adapted for operative placement and connection with a docking station whereby data collected during use can be downloaded and the battery can be recharged.

* * * * *

UNITED STATES PATENT AND TRADEMARK OFFICE
CERTIFICATE OF CORRECTION

PATENT NO. : 10,067,112 B2
APPLICATION NO. : 14/871761
DATED : September 4, 2018
INVENTOR(S) : Z. Daniel Deng et al.

It is certified that error appears in the above-identified patent and that said Letters Patent is hereby corrected as shown below:

(56) References Cited:

Replace - "CN 2014800479315 9/1994" with --CN 2014800479315 7/2017--

Replace - "8,485,985 B2 6/2013 Nagano et al." with --8,465,985 B2 10/2013 van Straaten--

Replace - "Barns, "Differences in Performance of Naturally and Artificially Propagated Sockeye Salmon Migrant Fry, as Measured with Swimming and Predation Tests", Journal of the Fisheries Board of Canada 24(5), 1967, Canada, pp. 1117-1153." with --Bams, "Differences in Performance of Naturally and Artificially Propagated Sockeye Salmon Migrant Fry, as Measured with Swimming and Predation Tests", Journal of the Fisheries Board of Canada 24(5), 1967, Canada, pp. 1117-1153.--

Replace - "Deng et al., U.S. Appl. No. 15/393,617, filed Dec. 29, 2016, titled "Systems and Methods far Monitsring Organisms Within an Aquatic Environment", 49 pages." with --Deng et al., U.S. Appl. No. 15/393,617, filed Dec. 29, 2016, titled "Systems and Methods for Monitoring Organisms Within an Aquatic Environment", 49 pages.--

Replace - "Fisheries and Oceans Canada (DFO), "Recovery Patentiai Assessment of American Eel (Anguilla rostrata) in Eastern Canada", Canadian Science Advisory Segretariat Science Advisory Report 2013/078, 2013, Canada, 65 pages." with --Fisheries and Oceans Canada (DFO), "Recovery Potential Assessment of American Eel (Anguilla rostrata) in Eastern Canada", Canadian Science Advisory Segretariat Science Advisory Report 2013/078, 2013, Canada, 65 pages.--

Replace - "Janak et al., "The Effects of Neutrally Buoyant, Externally Attached Transmitters on Swimming Performance and Predatar Avoidance of Juvenile Chinook Salmon", Transactians of the American Fisheries Society 141, 2012, United States, pp. 1424-4432." with --Janak et al., "The Effects of Neutrally Buoyant, Externally Attached Transmitters on Swimming Performance and Predator Avoidance of Juvenile Chinook Salmon", Transactions of the American Fisheries Society 141, 2012, United States, pp. 1424-4432.--

Signed and Sealed this
Third Day of September, 2019

Andrei Iancu
*Director of the United States Patent and Trademark Office*

CERTIFICATE OF CORRECTION (continued)
U.S. Pat. No. 10,067,112 B2

Replace - "Ward et al, "A Laboratory Evaluation of Tagging-Related Mortatlity and Tag Loss in Juvenile Humpback Chub", North American Journal of Fisheries Management 35, 2015, United States, pp. 135-140." with --Ward et al, "A Laboratory Evaluation of Tagging-Related Mortality and Tag Loss in Juvenile Humpback Chub", North American Journal of Fisheries Management 35, 2015, United States, pp. 135-140.--

Column 4, Line 10 - Replace "the sensors (26," with --the sensors 26,--

Column 8, Line 30 - Replace "26 to that" with --26 so that--

Column 11, Line 37 - Replace "the senor fish" with --the sensor fish--

Column 11, Line 38 - Replace "Senor Fish" with --Sensor Fish--

Column 13, Line 1 - Replace "The senor fish" with --The sensor fish--

Column 13, Line 12 - Replace "The senor fish" with --The sensor fish--